United States Patent [19]

Pohlman et al.

[11] Patent Number: 5,965,617
[45] Date of Patent: Oct. 12, 1999

[54] METHOD AND COMPOSITION FOR CONTROLLING MICROBIAL GROWTH USING BROMONTROSTYENE AND PERACETIC ACID

[75] Inventors: John L. Pohlman, Skokie; Timothy J. Hamilton, Gurnee, both of Ill.

[73] Assignee: ANGUS Chemical Company, Buffalo, Ill.

[21] Appl. No.: 09/057,716

[22] Filed: Apr. 9, 1998

Related U.S. Application Data

[60] Provisional application No. 60/073,565, Feb. 2, 1998.
[51] Int. Cl.$^6$ .......................... A61K 31/19; A61K 31/04
[52] U.S. Cl. .......................... 514/557; 514/740; 514/741
[58] Field of Search .................... 514/557, 740, 514/741

[56] References Cited

U.S. PATENT DOCUMENTS

| | | | |
|---|---|---|---|
| 3,629,465 | 12/1971 | Manowitz | 424/349 |
| 3,898,343 | 8/1975 | Swered et al. | 424/302 |
| 4,579,665 | 4/1986 | Davis et al. | 210/755 |
| 4,859,708 | 8/1989 | Donofrio et al. | 514/727 |
| 4,916,164 | 4/1990 | Whitekettle et al. | 514/665 |
| 4,966,775 | 10/1990 | Donofrio et al. | 424/661 |
| 5,015,660 | 5/1991 | Hidaka et al. | 514/441 |
| 5,063,212 | 11/1991 | Donofrio et al. | 514/75 |
| 5,198,453 | 3/1993 | LaZonby et al. | 514/367 |
| 5,256,419 | 10/1993 | Roe et al. | 424/407 |
| 5,306,432 | 4/1994 | Puetz | 210/759 |
| 5,324,432 | 6/1994 | Robertson et al. | 210/632 |
| 5,368,749 | 11/1994 | LaZonby | 210/756 |
| 5,395,530 | 3/1995 | Robertson et al. | 210/632 |
| 5,494,588 | 2/1996 | LaZonby | 210/755 |
| 5,624,575 | 4/1997 | Meade et al. | 210/759 |
| 5,658,467 | 8/1997 | Lazonby et al. | 210/754 |
| 5,785,867 | 7/1998 | LaZonby et al. | 210/759 |

OTHER PUBLICATIONS

Milanova, E., et al., Acute Toxicity to Fish and Solution Stability of Some Biocides Used in the Pulp and Paper Industry, Wat. Sci. Tech. vol. 35, No. 2–3, pp. 373–380, 1997.

Friend, P.L., et al., Biocides and Water Cooling Towers, Developments in Industrial Microbiology, Proceedings of the Thirty–Sixth General Meeting of the Society for Industrial Microbiology, vol. 21, pp. 123–131, Aug. 11–17, 1979.

*Primary Examiner*—S. Mark Clardy
*Assistant Examiner*—Sabiha N. Qazi
*Attorney, Agent, or Firm*—Arnold, White & Durkee

[57] ABSTRACT

The present invention provides a method and composition for controlling the growth of microorganisms in aqueous systems, such as industrial process waters. The method includes the steps of adding a synergistically effective amount of a biocide, 2-bromo-2-nitrostyrene ("BNS"), and an oxidant, peracetic acid, to industrial process waters to control microorganism growth. The composition of the present invention comprises a synergistically effective amount of a biocide, 2-bromo-2-nitrostyrene, and an oxidant, peracetic acid, to control microorganism growth. The method and composition of the present invention are particularly effective in the treatment of pulp and paper water processing systems.

16 Claims, 1 Drawing Sheet

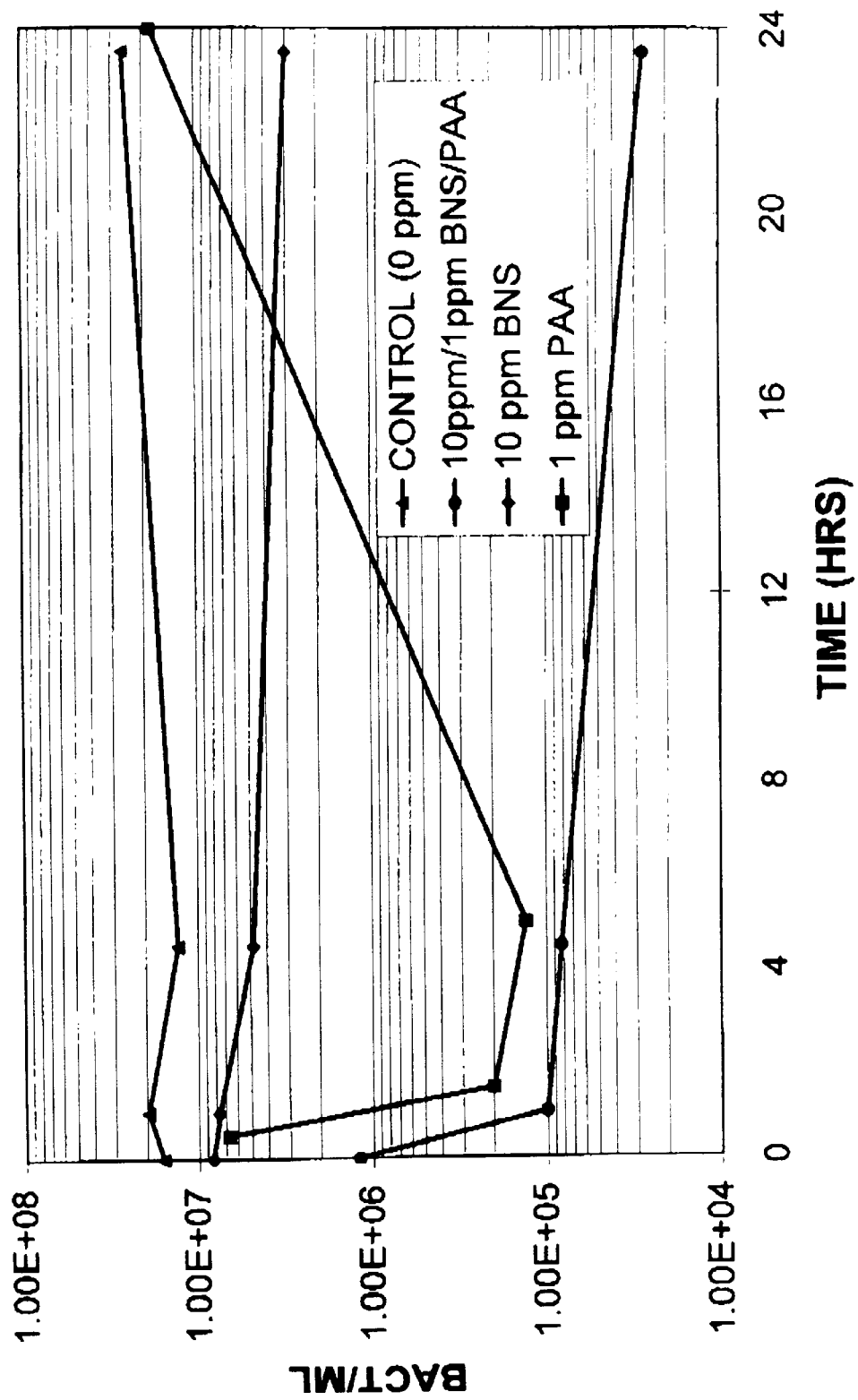

METHOD AND COMPOSITION FOR CONTROLLING MICROBIAL GROWTH USING BROMONTROSTYENE AND PERACETIC ACID

CROSS-REFERENCE TO RELATED APPLICATIONS

This application claims the benefit of copending Provisional patent application Ser. No. 60/073,565 filed Feb. 2, 1998 entitled "Method And Composition For Controlling Microbial Growth Using Bromonitrostyrene And Peracetic Acid."

BACKGROUND OF THE INVENTION

1. Field of the Invention

The present invention relates generally to controlling and inhibiting the growth of microorganisms in various types of aqueous systems. More specifically, it concerns methods and compositions for inhibiting the growth of microorganisms in industrial process waters and, in particular, in pulp and paper water processing systems.

2. Description of Related Art

A major problem in industrial manufacturing is control in the growth of microorganisms in aqueous systems, especially industrial process waters. Industrial process water includes pulp and paper process water, cooling tower water, waste water, food processing water, mineral slurries, air wash water, etc.

In pulp and paper water processing systems, the warm temperatures and the high carbohydrate content result in the constant growth of microorganisms. The presence of these microorganisms presents various difficulties for paper processors. The slime caused by the presence of microorganisms results in the formation of deposits. Slime can be defined as an "accretion or accumulation caused by certain microorganisms in the presence of pulp fiber, filler, dirt and other materials, mixed in varied proportions, having variable physical characteristics and accumulating at continuously changing rates."Safade, *Tackling the Slime Problem in a Paper Mill,* PTI, p. 280 (September 1988). The deposits which form cause fouling, plugging, clogging, system corrosion, and breakdowns of the paper machines which result in lost production time due to work stoppages. The breaking off of loose deposits causes defective, unsalable end products which result in an economic loss for the manufacturer.

In cooling tower water, growth of microorganisms can result in loss of heat transfer efficiency, clogged tubes, and corrosion.

In mineral slurries, microorganisms can lead to discoloration and can cause odor problems. Microbiological contamination can render mineral slurries unsalable, leading to economic loss for the manufacturer.

Industrial manufacturers have conventionally dealt with these problems by applying biocides to the process waters. Biocides are typically divided into two types: oxidizing biocides such as chlorine, bromine, chlorine dioxide, ozone, and peracetic acid; and non-oxidizing biocides such as isothiazolin, methylene bisthiocyanate, glutaraldehyde, quaternary ammonium compounds, DBNPA, and bromonitrostyrene. Both types of biocides operate on microorganisms by attacking the cell wall, the cytoplasmic membrane or the cellular constituents. Although individual biocides are sometimes used by themselves, there are numerous literature references disclosing the benefits of using synergistic combinations of biocides. The benefits of synergistic combinations include reduced use rates of biocides and broader spectrum of activity, i.e., such combinations are effective against a larger number of microorganisms than each of the individual biocides alone.

Numerous references disclose the use of bromonitrostyrene with other industrial biocides for control of microbial growth. For example, U.S. Pat. No. 5,063,212 (Donofrio et al.) discloses the use of bromonitrostyrene and a biocide, such as n-tributyltetradecylphosphonium chloride. U.S. Pat. No. 4,916,164 (Whitekettle et al.) discloses the use of bromonitrostyrene and a biocide, such as 2-(decylthio)ethanamine hydrochloride. U.S. Pat. No. 4,859,708 (Donofrio et al.) discloses the use of bromonitrostyrene and a biocide, such as 2-bromo-2-nitropropane-1,3-diol. U.S. Pat. No. 3,898,343 (Swered et al.) discloses the use of bromonitrostyrene and a biocide, such as methylene bisthiocyanate.

Numerous references disclose the use of peracetic acid with other industrial biocides for control of microbial growth. For example, U.S. Pat. No. 5,368,749 (LaZonby) discloses the use of sufficient amounts of an oxidant, such as peracetic acid, and glutaraldehyde. U.S. Pat. No. 4,966,775 (Donofrio et al.) discloses the use of 2-bromo-2-nitropropane-1,3 diol and an oxidizing biocide, such as peracetic acid. U.S. Pat. No. 5,494,588 (LaZonby) discloses the use of an oxidant, peracetic acid, and a biocide, such as isothiazolin, methylene bisthiocyanate, glutaraldehyde, DBNPA, carbamate, quaternary ammonium compounds, 4,5-dichloro 1,2 dithio-3-one, and 4,5-dichloro-2-N-octyl-4-isothiazolin-3-one or mixtures of such biocides. U.S. Pat. No. 5,658,467 (LaZonby et al.) discloses the use of an oxidant, peracetic acid, and a biocide, such as isothiazolin, methylene bisthiocyanate, glutaraldehyde, DBNPA, carbamate, quaternary ammonium compounds, 4,5-dichloro 1,2 dithio-3-one, 4,5-dichloro-2-N-octyl-4-isothiazolin-3-one, decylthioethylamine, orthophthaldehyde, 2-bromo-2-nitropropane-1,3-diol, 4,5-dichloro- 1,2-dithiol-3-one, dodecylguanidine hydrochloride, 1-(3-chloroallyl)-3,5,7-triaza-1-azoniaadamantane chloride, dibromo dicyanobutane and bis(trichloromethyl)sulfone or mixtures of such biocides. However, none of these references disclose the combination of bromonitrostyrene and peracetic acid.

SUMMARY OF THE INVENTION

The present invention discloses an improved method and composition for controlling and inhibiting the growth of microorganisms in aqueous systems, especially industrial process waters such as cooling tower water, mineral slurries, waste water, food processing water, air wash water, etc. The present invention is particularly effective in controlling microorganism growth in pulp and paper water processing systems. The method for controlling the growth of microorganisms of the present invention involves adding to the waters a synergistically effective amount of a biocide, 2-bromo-2-nitrostyrene ("BNS"), and an oxidant, peracetic acid, to control microorganism growth. The composition of the present invention comprises a synergistically effective amount of BNS and peracetic acid to control microorganism growth. In one embodiment, BNS and peracetic acid are used to control the growth of microorganisms in pulp and paper water processing systems. The method and composition of the present invention exhibit an unexpected synergistic activity against microorganisms.

An advantage of the present invention is that the combination of BNS and peracetic acid exhibits synergistic activity and, thus, enhanced biocidal efficacy, thereby lowering the amounts of expensive chemicals needed to control microorganism growth.

A further advantage of the present invention is that the BNS/peracetic acid combination provides a cost effective means for controlling microorganism growth.

Another advantage of the present invention is that the BNS/peracetic acid combination does not undergo a rapid reduction in its level of biocidal efficacy, thereby avoiding the need to add the chemicals frequently and the need to maintain multiple addition points throughout the system being treated.

A further advantage of the present invention is that the enhanced biocidal efficacy of the BNS and peracetic acid combination eliminates the need to add large initial doses of chemicals in order to compensate for the reduction in biocidal efficacy.

A further advantage of the present invention is that the BNS/peracetic acid combination is long lasting.

Another advantage of the present invention is that the BNS/peracetic acid combination is environmentally safe because only small doses are needed to effectively control microorganism growth. Furthermore, BNS and peracetic acid can be disposed of without adverse affects on the environment.

An additional advantage is that the method and composition of the present invention provide quick kill of the microorganisms present in the industrial process waters being treated.

DESCRIPTION OF DRAWING

FIG. 1 compares the bacterial counts in a paper mill white water for BNS and peracetic acid with the combination of both BNS and peracetic acid.

FIG. 2 is similar to FIG. 1, except that the ratio of BNS to peracetic acid is different.

DETAILED DESCRIPTION OF THE INVENTION

The present inventors have developed an improved method and composition for controlling the growth of microorganisms which comprises 2-bromo-2-nitrostyrene ("BNS") and peracetic acid. The method and composition of the present invention comprise a synergistically effective amount of BNS and peracetic acid for controlling microorganism growth.

The compound 2-bromo-2-nitrostyrene ("BNS")

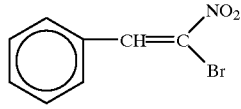

is a microbial growth inhibitor which is effective in controlling the growth of bacteria, slime and fungi in aqueous systems. BNS hydrolyzes quickly in water and the hydrolysis products are biocidal. The use of BNS in aqueous systems against a broad spectrum of microorganisms is disclosed in U.S. Pat. No. 3,629,465 (Manowitz et al.). BNS is highly effective against a broad spectrum of microbe species, such as Gram positive bacteria (i.e., staphylococcus aureus, staphylococcus epidermidis, streptococcus faecalis, streptococcus agalactiae); Gram negative bacteria (i.e., escherichia coli, pseudomonas aeruginosa, proteus vulgaris, aerobacter aerogenes, salmonella typhosa); yeasts (i.e., candida albicans, saccharomyces cerevisiae); molds (i.e., penicillium piscarium, penicillium funiculosum, aspergillus niger, aspergillus flavus, trichophyton mentagrophytes); and algae (i.e., chlorella vulgaris, chlamydomonas pseudagloe, scenedesmus naegelii). *Pseudomonas aeruginosa* and aspergillus niger are two examples of the many microorganisms that are commonly found in industrial process waters. BNS can be obtained from Angus Chemical Company.

Peracetic acid is an oxidant which is represented by the formula $$H_3COOOH$$

For approximately the last five years, peracetic acid has been used in controlling the growth of microorganisms in pulp and paper water processing systems. However, peracetic acid has been extensively used in other types of industrial process waters for a longer period of time. Peracetic acid is available from a number of chemical suppliers such as FMC Corporation.

Surprisingly, the present inventors have discovered that the combination of BNS and peracetic acid exhibits synergistic activity. Although BNS and peracetic acid are known compounds, the synergistic effect obtained by combining BNS and peracetic acid has not been disclosed previously. Synergistic activity exists where the total effect of the active components in a mixture is greater than the sum of the individual components. Surprisingly, the present inventors have found that when BNS and peracetic acid are combined in certain instances, the resultant combination exhibits a greater level of control of microorganism growth than that exhibited by BNS and peracetic acid individually. Due to the BNS/peracetic acid combination's enhanced ability to control microorganism growth, the dosages of BNS and peracetic acid individually and the dosage of the BNS/peracetic acid combination which are necessary to control microorganism growth is reduced.

The method for controlling the growth of microorganisms of the present invention involves adding to the waters a synergistically effective amount of BNS and peracetic acid to control microorganism growth. The method is effective in controlling the growth of microorganisms in pulp and paper water processing systems. The method of controlling the growth of microorganisms in aqueous systems according to the present invention comprises the steps of adding BNS and peracetic acid to the aqueous system. In an embodiment, BNS and peracetic acid are separate components for addition to the system.

In a preferred embodiment, peracetic acid is added to the aqueous system prior to the addition of BNS. In one embodiment, peracetic acid is added 30 minutes before adding BNS to the system to allow for contact time between the peracetic acid and the microorganisms. The BNS and peracetic acid can be added to the aqueous system by any method which is capable of producing the desired concentration of each compound in the waters.

The composition of the present invention comprises a synergistically effective amount of BNS and peracetic acid to control microorganism growth. The composition is effective in controlling the growth of microorganisms in pulp and paper water processing systems.

The amount of BNS and peracetic acid necessary to control the growth of microorganisms varies depending on the aqueous system being treated. The concentration of BNS can range from about 1 part per million (ppm) by weight (mg/kg) to 200 ppm of active BNS. The concentration of peracetic acid can range from about 0.1 ppm to 25 ppm by weight (mg/kg) of active peracetic acid. In one embodiment, BNS and peracetic acid are present in a range from about 5 to 50 ppm of active BNS and from about 0.25 to 5 ppm of active peracetic acid. In a further embodiment, BNS and peracetic acid are present in a range from about 10 to 20 ppm of active BNS and from about 0.5 to 2 ppm of active peracetic acid. In another embodiment, BNS is present at about 10 ppm of active BNS and peracetic acid is present in a range from about 0.5 to 1 ppm of active peracetic acid.

BNS and peracetic acid are obtainable at different usable concentration levels, or activity levels. The BNS used in the following example is 25% active while the peracetic acid is 5% active. Therefore, in the following example, biocide concentration is quoted in terms of active ingredient.

The following example illustrates the synergistic relationship obtained with the compositions of the present invention.

Synergy can be shown mathematically by an industry accepted method which is described by Kull et al. in *Applied Microbiology*, vol. 9, pages 538–41 (1961). As applied to this invention, the components are defined as follows:

$Q_A$=the ppm of active BNS alone which produces an endpoint.

$Q_B$=the ppm of active peracetic acid alone which produces an endpoint.

$Q_a$=the ppm of active BNS, in combination with peracetic acid, which produces an endpoint.

$Q_b$=the ppm of active peracetic acid, in combination with BNS, which produces an endpoint.

An endpoint is an arbitrarily selected point which is characterized by a desired reduction in the level of microorganisms present in the process water containing an added biocide (ie., treated water) relative to the same process water with no added biocide (i.e., untreated water). The untreated water in this example is labeled as the control.

Synergy is defined as $$Q_a/Q_A + Q_b/Q_B = \text{Synergy Index}$$

If the resulting Synergy Index is

<1, synergy exists;
=1, additivity exists;
>1, antagonism exists.

The following test procedures were used during the experimentation of the present invention.

Process water was obtained from a commercial paper mill and is commonly known as "white" or "process" water. The water (pH =7.7) was divided into aliquots and treated with the indicated concentrations of peracetic acid ("PAA") (5% active obtained from FMC Corporation). After 30 minutes of contact time, the indicated concentrations of BNS (25% active) were added to the aliquots of water which were previously treated with peracetic acid. The aliquots were held at room temperature. Samples were taken from the aliquots and tested for microbial survival at the designated times shown below. Microbial survival is the total number of viable organisms measured in colony forming units per milliliter (CFU/mL) on Tryptone Glucose Extract (TGE) agar plates. In the present example, the TGE agar plates were incubated for 48 hours at 35 ° C. A control containing no BNS or peracetic acid was also run for comparison, the results of which are shown below. An endpoint of 2 $\log_{10}$ reduction in viable organisms was selected for calculating synergy. The reduction in viable organisms is determined by comparing a given treated sample with the untreated control sample at the same time.

EXAMPLE 1

Synergistic activity against microorganisms was demonstrated in paper mill white water at a pH of 7.7. The data obtained is shown in the table below and in FIGS. 1 and 2.

| Biocide | active (ppm by weight) | Microbial Survival At Specified Time | | | |
| --- | --- | --- | --- | --- | --- |
| | | 30 min CFU/mL | 90 min CFU/mL | 5 hrs CFU/mL | 24 hrs CFU/mL |
| PAA | 0.5 | 1.10E + 0.7 | 1.50E + 07 | 1.60E + 07 | 2.40E + 07 |
| PAA | 1 | 6.70E + 06 | 2.00E + 05 | 1.30E + 05 | 1.80E + 07 |
| PAA | 2 | 1.90E + 06 | 1.30E + 05 | 1.60E + 05 | 1.70E + 07 |

| Biocide | active (ppm by weight) | Microbial Survival At Specified Time | | | |
| --- | --- | --- | --- | --- | --- |
| | | 0 min CFU/mL | 60 min CFU/mL | 4.5 hrs CFU/mL | 23.5 hrs CFU/mL |
| BNS | 100 | 6.20E + 06 | 2.40E + 06 | 1.70E + 05 | 8.70E + 04 |
| BNS | 50 | 7.30E + 06 | 4.00E + 06 | 6.70E + 05 | 1.80E + 05 |
| BNS | 25 | 7.70E + 06 | 4.60E + 06 | 9.50E + 05 | 5.20E + 05 |
| BNS | 10 | 8.30E + 06 | 7.60E + 06 | 4.80E + 06 | 3.00E + 06 |
| BNS/PAA | 10/0.5 | 8.10E + 06 | 2.80E + 06 | 2.40E + 06 | 2.40E + 05 |
| BNS/PAA | 10/1 | 1.20E + 06 | 9.70E + 04 | 8.20E + 04 | 2.70E + 04 |
| Control | 0 | 1.60E + 07 | 1.80E + 07 | 1.30E + 07 | 2.60E + 07 |

After 5 hours of contact, a 2 $\log_{10}$ drop is achieved with:
PAA = 2 ppm
BNS = 100 ppm
PAA/BNS = 10 ppm/1 ppm
QA = 100 ppm; $Q_B$ = 2 ppm; $Q_a$ = 10 ppm and $Q_b$ = 1 ppm. Thus, SI = 10/100 + ½ = 0.6.
Since 0.6 is <1, the BNS and peracetic acid combination demonstrated synergy.
After 24 hours of contact, a 2 $\log_{10}$ drop is achieved with:
PAA > 2 ppm (4 ppm)
BNS = 25 ppm
PAA/BNS = 10 ppm/0.5 ppm After 5 hours of contact, a 2 $\log_{10}$ drop is achieved with:

PAA=2 ppm

BNS=100 ppm

PAA/BNS=10 ppm/1 ppm $Q_A$=100 ppm; $Q_B$=2 ppm; $Q_a$=10 ppm and $Q_b$=1 ppm. Thus, SI=10/100+½=0.6. Since 0.6 is <1, the BNS and peracetic acid combination demonstrated synergy.

After 24 hours of contact, a 2 $\log_{10}$ drop is achieved with:

PAA>2 ppm (4 ppm)

BNS=25 ppm

PAA/BNS=10 ppm/0.5 ppm $Q_A$=25 ppm; $Q_B$=4 ppm; $Q_a$=10 ppm and $Q_b$=0.5 ppm. Thus, SI=10/25+0.5/4=0.525. Since 0.525 is <1, the BNS and peracetic acid combination demonstrated synergy. The value of 4 ppm is used by way of example only. Any concentration of peracetic acid greater than 2 ppm will demonstrate synergy using the above formulation. As the value for $Q_B$ increases, the value for $Q_b/Q_B$ decreases. Thus, as the peracetic acid concentration increases, the overall value for $Q_b/Q_B$ to be used in determining the Synergy Index decreases. The net result is that the value inserted for $Q_B$ with a peracetic acid concentration greater than 2 ppm has little effect on the calculation of the Synergy Index.

As can be seen in the above example, peracetic acid alone is ineffective in reducing the microorganism level in a 24 hour period. BNS alone reduces the level of microorganisms in a 24 hour period; however, large amounts of BNS are required in order to produce a significant reduction over a 24 hour period. The data shows that 100 ppm of BNS is required to exhibit a 3 $\log_{10}$ reduction and that 50 ppm is required to exhibit a 2 $\log_{10}$ reduction in the level of microorganisms. In contrast to the reduction seen with the addition of BNS or peracetic acid individually, a small amount of BNS and peracetic acid together produces a significant reduction in the level of microorganisms over a 24 hour period. The data shows that the combination of only 10 ppm of BNS and 1 ppm of peracetic acid produces a 3 $\log_{10}$ reduction over a 24 hour period. Furthermore, a combination of only 10 ppm of BNS and 0.5 ppm of peracetic acid produces a 2 $\log_{10}$ reduction in a 24 hour period. Thus, the BNS/peracetic acid combination clearly demonstrates synergy, showing an enhanced ability to reduce the microorganism level in process water in small doses.

What is claimed is:

1. A method for controlling the growth of microorganisms in aqueous systems comprising the steps of adding to the waters a synergistically effective amount of a biocide, 2-bromo-2-nitrostyrene, and an oxidant, peracetic acid.

2. The method of claim 1 wherein the aqueous system is an industrial process water system.

3. The method of claim 2 wherein the industrial process water system is a pulp and paper water processing system.

4. The method of claim 1 wherein the peracetic acid is added prior to the 2-bromo-2-nitrostyrene.

5. The method of claim 4 wherein the peracetic acid is added 30 minutes prior to the 2-bromo-2-nitrostyrene.

6. The method of claim 1 wherein the amount of 2-bromo-2-nitrostyrene ranges from about 1 to 200 ppm of active 2-bromo-2-nitrostyrene and the amount of peracetic acid ranges from about 0.1 to 25 ppm of active peracetic acid.

7. The method of claim 6 wherein the amount of 2-bromo-2-nitrostyrene ranges from about 5 to 50 ppm of active 2-bromo-2-nitrostyrene and the amount of peracetic acid ranges from about 0.25 to 5 ppm of active peracetic acid.

8. The method of claim 7 wherein the amount of 2-bromo-2-nitrostyrene ranges from about 10 to 20 ppm of active 2-bromo-2-nitrostyrene and the amount of peracetic acid ranges from about 0.5 to 2 ppm of active peracetic acid.

9. The method of claim 8 wherein the amount of 2-bromo-2-nitrostyrene is about 10 ppm of active 2-bromo-2-nitrostyrene and the amount of peracetic acid ranges from about 0.5 to 1 ppm of active peracetic acid.

10. An aqueous process water that comprises a synergistically effective amount of a biocide, 2-bromo-2-nitrostyrene, and an oxidant, peracetic acid, for controlling the growth of microorganisms in aqueous systems.

11. The aqueous process water of claim 10 wherein the aqueous system is an industrial process water system.

12. The aqueous process water of claim 11 wherein the industrial process water system is a pulp and paper water processing system.

13. The aqueous process water of claim 10 wherein the amount of 2-bromo-2-nitrostyrene ranges from about 1 to 200 ppm of active 2-bromo-2-nitrostyrene and the amount of peracetic acid ranges from about 0.1 to 25 ppm of active peracetic acid.

14. The aqueous process water of claim 13 wherein the amount of 2-bromo-2-nitrostyrene ranges from about 5 to 50 ppm of active 2-bromo-2-nitrostyrene and the amount of peracetic acid ranges from about 0.25 to 5 ppm of active peracetic acid.

15. The aqueous process water of claim 14 wherein the amount of 2-bromo-2-nitrostyrene ranges from about 10 to 20 ppm of active 2-bromo-2-nitrostyrene and the amount of peracetic acid ranges from about 0.5 to 2 ppm of active peracetic acid.

16. The aqueous process water of claim 15 wherein the amount of 2-bromo-2-nitrostyrene is about 10 ppm of active 2-bromo-2-nitrostyrene and the amount of peracetic acid ranges from about 0.5 to 1 ppm of active peracetic acid.

* * * * *

UNITED STATES PATENT AND TRADEMARK OFFICE
CERTIFICATE OF CORRECTION

PATENT NO. : 5,965,617

DATED : October 12, 1999

INVENTOR(S) : Pohlman et al.

It is certified that error appears in the above-identified patent and that said Letters Patent is hereby corrected as shown below:

```
Title page, item [54] and Col. 1, line 3,
```
   correct the spelling of the word "BROMONITROSTYRENE"

Signed and Sealed this

Fourteenth Day of March, 2000

Attest:

Q. TODD DICKINSON

Attesting Officer

Commissioner of Patents and Trademarks